United States Patent [19]

Pendergrass et al.

[11] Patent Number: 4,515,594

[45] Date of Patent: May 7, 1985

[54] SURGICAL SPONGE

[75] Inventors: John E. Pendergrass, Seneca; David T. Melton, Walhalla, both of S.C.

[73] Assignee: The Kendall Company, Boston, Mass.

[21] Appl. No.: 457,092

[22] Filed: Jan. 10, 1983

[51] Int. Cl.³ .............................................. A61F 13/16
[52] U.S. Cl. ..................................................... 604/384
[58] Field of Search ............... 604/384, 385, 379, 365; 128/156, 155

[56] References Cited

U.S. PATENT DOCUMENTS

| 2,081,370 | 5/1937 | Secrist | 604/384 X |
| 2,986,780 | 6/1961 | Bletzinger | 604/385 X |
| 3,214,323 | 10/1965 | Russell et al. | 604/384 X |

Primary Examiner—John D. Yasko
Attorney, Agent, or Firm—Frederick R. Cantor

[57] ABSTRACT

An improved surgical dressing or surgical sponge being a composite nonwoven and knitted fabric structure having high fluid absorbency and capillarity characteristics, is prepared by knitting a set of chain stitch wales of hydrophilic yarns, with said chain stitch wales being interconnected laterally by sets of filling courses, said filling course yarns being also comprised preferably of hydrophilic material. The chain stitch wale yarns are interknit through a light-weight, absorbent, non-woven web. The centrally disposed non-woven web is pliable and deformable so that capillary fibrous bundles of non-woven fabrics may be drawn into intimate physical contact with the yarns forming the loops of the chain stitch wales and their associated filling courses, resulting in a composite material having enhanced absorbancy and capillarity characteristics.

11 Claims, 4 Drawing Figures

SURGICAL SPONGE

BACKGROUND OF THE INVENTION

The present invention relates to surgical sponges and surgical and medical dressings.

The present invention relates more specifically to surgical sponges and surgical dressings incorporating light weight absorbent fabrics.

The present invention most particularly relates to a composite crochet knitted and light weight non-woven fabric, some of the non-woven fibers of which, are arranged into a complex configuration, resulting in enhanced capillarity through intimate physical contact with the knit chain-stitch loops formed from hydrophilic yarns.

There exists at the present time a need for a surgical sponge or surgical dressing material suitable for use in the surgical and medical fields, which incorporate highly desirable absorbancy and capillarity properties, and is also light in weight. The desirable properties are those particularly of high capillarity combined with increased absorbancy, with an enlarged capacity for retaining liquids, particularly aqueous wound liquids, such as blood, lymph, and the like.

Woven surgical gauze has been widely incorporated in surgical dressings in which absorbency is an important characteristic. Woven surgical gauze, utilizing cotton, or the like, is generally considered to be the safest absorbent material available for use in operative and post-operative procedures. It is also well recognized that it possesses certain disadvantages. Surgical gauze is an open mesh, loosely woven fabric, composed basically of absorbent cotton fibers tightly twisted into yarns. This physical arrangement of the absorbent fibers enhances the capillarity property, but reduces the total absorbent capacity originally possessed by the fibers when in a loosely associated state. Tests have shown that the total absorbent capacity of loosely associated fibers is several times that of the total absorbent capacity of the same fibers when they are in the tightly twisted state.

Furthermore, as an absorbent material, surgical gauze has the disadvantage of having its absorbent capacity non-uniformly distributed over a wide area, in part because its yarns are arranged relatively widely spaced, and also due, in part, to poorer capillarity characteristics. Thus, the absorbent fibers in the gauze are provided with very little opportunity to remove wound liquids uniformly and rapidly from a field of operation.

On the other hand, the use of the surgical gauze fibers in a loosly associated state is also objectionable, due, in part, to the tendency of the individual loosely-associated fibers to become detached from the total mass of fibers, and to then adhere to the wound, being referred to as "linting out". Furthermore, such a mass of loosely associated fibers would be difficult for a surgeon or nurse to readily manipulate. Likewise, the capillarity of a loosely associated mass of fibers is insufficient to cause absorbed liquids to spread uniformly laterally throughout the mass, resulting in the wound liquid quickly passing through to the back of the absorbent gauze mass.

Further, light weight nonwoven fabrics are generally superior than woven surgical gauze in their absorbency characteristics, in terms of grams of moisture absorbed per gram of fabric material employed. However, when nonwoven fabrics are produced in a weight that is equivalent to heavier surgical gauze, they lack dimensional stability.

In the present invention, by combining, and thereby reinforcing the light weight nonwoven fabric material with a crochet knitted fabric structure, we are able to produce a highly absorbent surgical sponge or dressing structure, having excellent wound liquid absorbtion, high capillarity, dimensional stability and wound conformity characteristics.

Other characteristics that are desirable to incorporate into an improved surgical sponge or dressing, and that are, in fact, some of the important attributes of the present invention, are low "linting out" levels, a high loft, and a gauze-like appearance. Further, the present invention is also characterized by being economical to manufacture and, therefore, highly competitive with surgical cotton gauze.

Further, the present invention surgical sponge material readily lends itself during manufacture to the incorporation of either a visual, or X-ray detectable filament-like element within the composite fabric structure of an exemplary embodiment of the present invention.

In U.S. Pat. No. 2,444,115, there is described a fabric wherein a fibrous web comprising a portion of thermoplastic fibers is bonded to an open-meshed fabric composed of textile yarns, by the use of heat and pressure to develop the adhesive properties of the thermoplastic fibers. Although such combinations are in many ways superior to woven gauze, the fibers in the nonwoven fabric are of uniform distribution, limiting the degree of capillary spread of fluid. The present invention is concerned with improvements in such lightweight absorbent fabrics.

In U.S Pat. No. 3,793,679, there is presented a description of the method of construction of a nonwoven web component similar to one that is utilized in the present invention.

U.S. Pat. No. 3,969,561 contains a description of a non-woven fabric construction and the method of making same, that is similar to the nonwoven fabric component of the present invention.

SUMMARY OF THE INVENTION

It is, therefore, an object of the present invention to provide an improved surgical sponge and surgical and medical dressing.

It is a further object of the present invention to provide an improved surgical sponge and surgical dressing incorporating lightweight absorbent fabrics.

It is yet another object of the present invention to provide an improved surgical dressing incorporating a composite crochet knitted and lightweight, non-woven fabric, having some nonwoven fibers arranged into a complex configuration, and resulting in a composite material having enhanced absorbance and capillarity characteristics, in part, through the knit chain stitch loops formed from hydrophilic yarns.

These and other objects of the present invention are accomplished in accordance with the illustrated exemplary embodiment of the present invention.

The improved surgical sponge or surgical dressing of the present invention with its incorporated fabric structure, having high fluid absorbancy and capillarity characteristics, is prepared by knitting a set of chain-stitch wales of hydrophilic yarns, with said wales being interconnected laterally by sets of filling courses, also comprised preferably of hydrophilic yarns. In the formation of these fabrics, the needles governing the wale yarns and filling courses are caused to pass through a lightweight, absorbent, nonwoven web, the nonwoven web preferably being of from 6 to 10 grams per square yard in weight. The nonwoven web is of a pliable and deformable nature, so that bundles of nonwoven fibers may be readily drawn, without breakage, into bunched configurations and being in intimate physical contact with the crochet knit yarns forming the loops of the chain-stitch wales and their associated filling courses. In this manner, a lightweight, composite absorbent fabric is formed, with enhanced capillarity and capacity of absorbing and retaining liquids, due, in large part, to the interaction of the crochet knit yarns and the associated nonwoven fibers.

BRIEF DESCRIPTION OF THE DRAWINGS

In order that the present invention may be more fully and readily understood, and so that further features thereof may be appreciated, the invention will now be described by way of example with reference to the accompanying drawings, in which like reference characters are used throughout in order to designate like parts, and in which.

DETAILED DESCRIPTION OF THE PREFERRED EMBODIMENT

Figure 1:
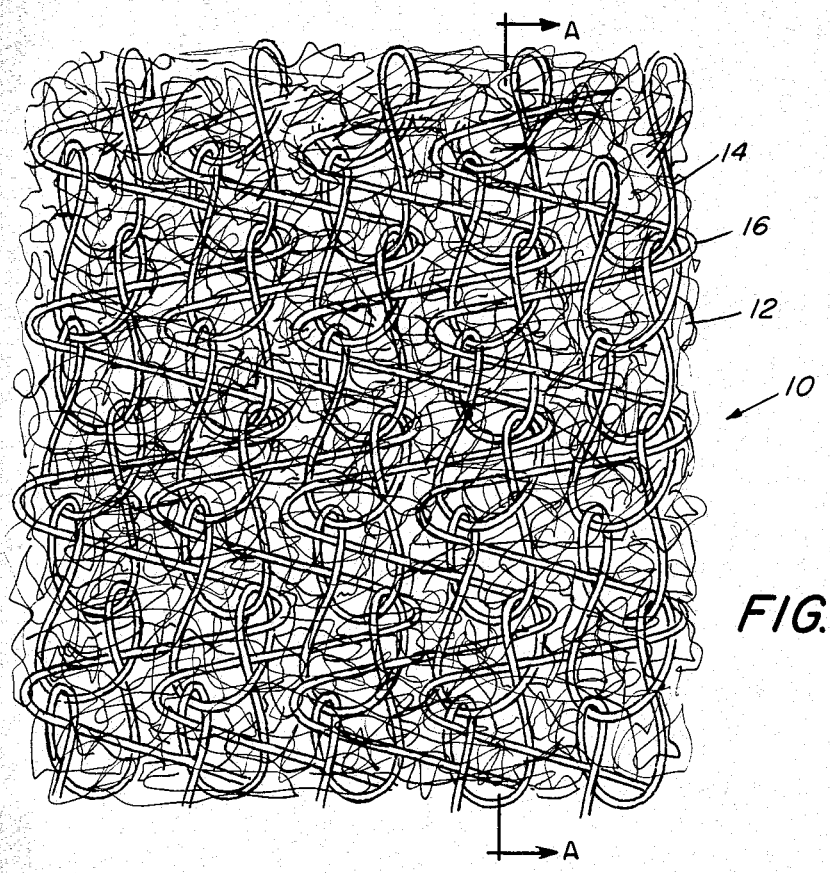
FIG. 1 is an enlarged diagrammatic plan view of a partial segment of the composite fabric construction of an exemplary embodiment of the present invention.

Referring now to FIG. 1, which is an enlarged diagrammatic plan view of a partial segment of the composite fabric construction of an exemplary embodiment of the present invention.

The partial segment of the fabric composite of the surgical dressing is depicted here generally as 10. The nonwoven component, depicted here as 12, comprises a randomly-arranged gossamer, or thin, gauze-like material, that is produced by depositing fibers onto a screen by means of air-laid methods. The fibers of the nonwoven web component 12, of the present invention, are preferably hydrophilic in nature, and further, preferably may be a rayon, or the like, cellulosic material, but may include proportions of hydrophobic fibers blended therein. In variant embodiments of the present invention, cotton may also be the cellulosic non-woven material that is employed or blends thereof.

It should further be emphasized, that regardless of the composition of the nonwoven web component 12 that is to be utilized, it is essential that in order to obtain suitable high absorbancy and capillarity characteristics of the present invention, an efficient hydrophilic material should be chosen.

In the present invention, hydrophilic rayon or cotton fibers or the like, having a weight of from 6 to 10 grams per square yard were utilized for the nonwoven component. This lightweight nonwoven is advantageously of a randomized orientation, and may be made by air-lay techniques such as described in U.S. Pat. No. 3,793,679.

The crochet knit component of the present invention, comprises hydrophilic knit yarns in the warp, that are arranged essentially in two different configurations.

The crochet knot components are further overknit into the nonwoven web component 12 thereby forming the fabric composite 10.

One set of crochet knit warp yarns, depicted here as 14, is arranged in a series of chain stitch wales. Another set of crochet knit warp yarns, depicted here as 16, are filling courses. The chain-stitch warp yarns 14 are interconnected laterally by sets of the filling yarns 16. The filling yarns 16 are comprised preferably of hydrophilic yarns, such as rayon, cotton, or the like, cellulosic material.

It is to be noted that other crochet knit stitch patterns may be utilized in various embodiments of the present invention.

Figure 2:
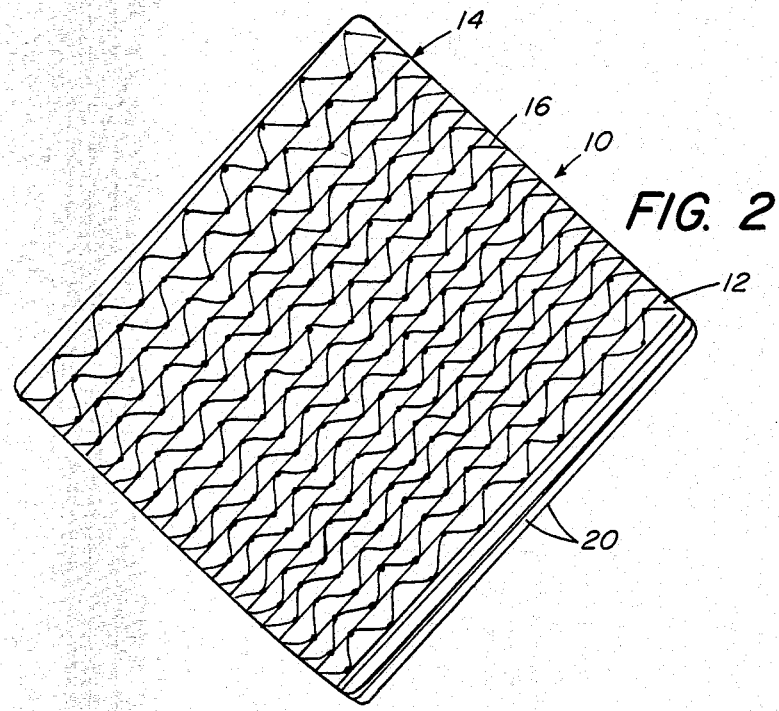
FIG. 2 is an isometric view of an exemplary embodiment of the present invention shown folded upon itself into a multi-layered surgical dressing.

FIG. 2 is an isometric view of an exemplary embodiment of the present invention shown folded upon itself into a multi-layered surgical dressing. The surgical sponge is formed by the folding of a large layer of the fabric composite 10. The multiple folded layers are depicted here as 20 on FIG. 2.

The above-described warp yarns 14, interlace together with, and are partly held in place by, sets of filling yarns 16, which are arrayed in a regular repetitive pattern across the warp yarns 14. The filling yarns 16 are essentially of a non-stretch nature, being preferably spun yarns of hydrophilic rayon or cotton.

In some applications it may be possible to substitute a hydrophobic material for the warp and/or filling yarns in a variant embodiment of the invention.

Figure 4:
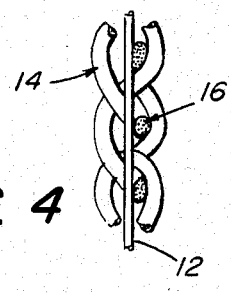
FIG. 4 is a diagrammatic cross-sectional view of an exemplary embodiment of the present invention taken through lines A—A of FIG. 1.

FIG. 4 is a diagrammatic cross-sectional view of an exemplary embodiment of the present invention, taken through Lines A—A of FIG. 1.

By maintaining proper tension of the non-woven component 12 during construction, it is possible during construction to penetrate the nonwoven fabric component 12 with the crochet knitting needles, thereby forming the composite surgical sponge construction. This penetration of the non-woven web component 12 does not restrict the normal production or patterning possibilities of the crochet knitting machine.

As the crochet needle moves forward, it penetrates the non-woven web leaving the previously formed warp stitch on the back side of the web. The warp needle then receives additional yarn. The warp yarn is then carried back through the non-woven material 12 as the needle returns to the withdrawn position.

This horizontal displacement of the needle and warp yarn results in the surgical sponge composite structure with the nonwoven fabric 12 being sandwiched or centrally-disposed between the crochet knit warp yarns 14, 16.

It is to be noted that the filling pattern utilized in the present invention results in the filling interlacing every warp crochet knit needle. It is also possible to produce the same pattern with more needles removed, or none of the needles removed between the warp ends. The removing of needles reduces the number of warp ends required, and, thereby, the composite fabric construction weight per unit area also decreases.

Figure 3:
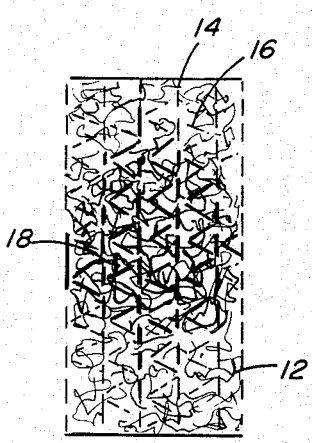
FIG. 3 is an enlarged fragmentary view of a segment of the fabric construction of the present invention showing the cooperative absorbency of yarns and nonwoven fibers when in contact with liquids.

FIG. 3 is an enlarged fragmentary view of a segment of the fabric construction of the present invention showing the cooperative absorbency of yarns and nonwoven fibers when in contact with liquids.

The particular fiber arrangement composite in the crochet knitted fabric of the present invention allows for better absorbance of liquids such as blood, lymph, or the like, emerging from a wound. Wound liquids are depicted in FIG. 3 as 18. The formation of the chain-stitch loops 14 and the filling courses 16 provides a plurality of capillary fibrous bundles (not numbered), resulting in additional capillary spaces in the composite fabric, which aids in the rapid and uniform absorbance of the wound liquids.

The term "capillary fibrous bundles" refers to the plurality of regions in the composite fabric where the nonwoven fiber component 12 is drawn into intimate physical contact with the intermittent crochet knit warp yarns 14 and 16. It is this intimate physical contact between the hydrophilic components of the composite structure that results in the enhanced absorbency and capillary characteristics of the present invention.

Laboratory tests have shown that the surgical sponge of the present invention has approximately 30 percent greater absorption capacity than that of a conventional surgical gauze sponge.

Furthermore, the composite fabric of the present invention transmits air through minute porosities in the nonwoven component 12, much more freely than the prior art woven fabrics, resulting usually in earlier wound healing than heretofore.

It is also envisioned, that due to the enhanced absorbency and capillarity characteristics of the fabric of the present invention, other possible applications for the composite fabric material will be developed. Floor sponges, eye pads, under-cast pads and wipes, are only a few of the many possible later applications.

The foregoing detailed description of the preferred embodiments of the present invention is given for purposes of clarity of understanding only, and no unnecessary limitations should be understood or implied therefrom, as modifications may be obvious to those skilled in the art.

What is claimed is:

1. A surgical dressing or surgical sponge material having enhanced absorbance and capillarity characteristics, comprising:
    a nonwoven fabric component; and a
    crochet knitted array component;
    said crochet knitted array component being interlaced in intimate physical contact by means of stitching through said centrally-disposed nonwoven fabric component.

2. The surgical dressing or surgical sponge material of claim 1, wherein said nonwoven fabric component comprises a randomly oriented, lightweight, essentially hydrophilic material.

3. The surgical dressing or surgical sponge material of claim 2, wherein said nonwoven fabric component is produced by randomly depositing said hydrophilic fibers onto a screen by means of air-lay methods.

4. The surgical dressing or surgical sponge material of claim 1, wherein said crochet knitted array component is comprised of a hydrophilic yarn.

5. The surgical dressing or surgical sponge material of claim 4, wherein said hydrophilic yarn material is rayon.

6. The surgical dressing or surgical sponge material of claim 4, wherein said hydrophilic yarn material is cotton.

7. The surgical dressing or surgical sponge material of claim 4, wherein said hydrophilic yarn is preferably a cellulosic material.

8. The surgical dressing or surgical sponge material of claim 1, wherein said crochet knitted array component comprises a pattern of chain stitch wales and filling courses.

9. The surgical dressing or surgical sponge material of claim 8, wherein said chain stitch wales and filling courses are interlaced and are in intimate physical contact with said centrally-disposed non-woven fabric component.

10. The surgical dressing or surgical sponge material of claim 8, wherein said pattern of chain stitch wales and filling courses includes a plurality of capillary fibrous bundles at the interfaces of the knitted components and the non-woven fabric.

11. The surgical dressing or surgical sponge material of claim 1, wherein said crochet knitted array component is comprised of a hydrophobic yarn.

* * * * *